(12) United States Patent
Mahalingam et al.

(10) Patent No.: US 8,121,804 B2
(45) Date of Patent: Feb. 21, 2012

(54) ELECTRICAL NETWORK ANALYSIS OF A MULTIPHASE SYSTEM

(75) Inventors: Sakethraman Mahalingam, Bangalore (IN); Arijit Banerjee, Bangalore (IN); Wrichik Basu, Bangalore (IN); Harish Kumar Pillai, Mumbai (IN)

(73) Assignee: General Electric Company, Niskayuna, NY (US)

( * ) Notice: Subject to any disclaimer, the term of this patent is extended or adjusted under 35 U.S.C. 154(b) by 58 days.

(21) Appl. No.: 12/652,120

(22) Filed: Jan. 5, 2010

(65) Prior Publication Data

US 2011/0166814 A1    Jul. 7, 2011

(51) Int. Cl.
*G01R 23/16* (2006.01)
*G01R 27/08* (2006.01)

(52) U.S. Cl. ......................................................... 702/77
(58) Field of Classification Search ...................... 702/77
See application file for complete search history.

(56) References Cited

U.S. PATENT DOCUMENTS

| | | | |
|---|---|---|---|
| 4,063,153 | A | 12/1977 | Dechene et al. |
| 4,975,645 | A | 12/1990 | Lucas |
| 5,291,791 | A | 3/1994 | Lucas et al. |
| 5,396,806 | A | 3/1995 | Dechene et al. |
| 7,167,009 | B2 | 1/2007 | van Schoor et al. |
| 2003/0016001 | A1 * | 1/2003 | Borup .......................... 323/364 |
| 2003/0085715 | A1 | 5/2003 | Lubkeman et al. |
| 2006/0265150 | A1 * | 11/2006 | Hu et al. .......................... 702/50 |
| 2007/0157737 | A1 * | 7/2007 | Gysling et al. ............. 73/861.23 |

OTHER PUBLICATIONS

Mohd. Zaid Abdul L AH; "Simulation of an Inverse Problem in Electrical Impedance Tomography Using Resistance Electrical Network Analogues"; Int. J. Elect. Enging. Educ., vol. 36, pp. 311-324. Manchester U.P., 1999. Printed in Great Britain.
J. H. Calderwood and E. R. Mognaschi; "A novel filed for possible use in medical impedance tomography"; Journal of Medical Engineering & Technology, 1998, vol. 22, No. 3, pp. 121-125.
Jun Gu, W Yin, Yannian Rui, Chao Wang, Huaxiang Wang; "A New Resistor Network Based Forward Model for Electrical Impedance Tomography Sensors"; I2MTC 2009—International Instrumentation and Measurement, Technology Conference, Singapore, May 5-7, 2009; 4 Pages.
D. C. Dobson et al., "Resolution and stability analysis of an inverse problem in electrical impedance tomography: dependence on the input current patterns," vol. 54, 1994, pp. 1542-1560.
J. H. Kim et al., "Directional algebraic reconstruction technique for electrical impedance tomography," Journal of the Korean Physical Society, vol. 54, No. 4, Apr. 2009, pp. 1439-1447.

* cited by examiner

*Primary Examiner* — Cindy H Khuu
(74) *Attorney, Agent, or Firm* — Ann M. Agosti

(57) ABSTRACT

A method for determining characteristics of a multi-material object is provided. The method includes determining an electric element matrix representing the multi-material object. The electric element matrix is pre-multiplied by a first mathematical transformation matrix to obtain a first transformed electric element matrix. The first transformed electric element matrix is post-multiplied with a second mathematical transformation matrix to obtain a second transformed electric element matrix. The method further includes determining the characteristics of the multi-material object based on the second transformed electric element matrix.

24 Claims, 8 Drawing Sheets

ELECTRICAL NETWORK ANALYSIS OF A MULTIPHASE SYSTEM

BACKGROUND

This invention relates generally to a method for determining the composition and characteristics of the individual materials within a multi-material object, and, more specifically, to a method of analyzing the electrical network representation of the multi-material object.

Multiphase flow is an example of a multi-material object in which at least two materials or phases are flowing together inside a pipe or a conduit. Multiphase flow processes are important to a variety of industries including, for example, petroleum, pharmaceutical, food, and chemical industries. There is a need for direct knowledge of the internal flow characteristics in these types of multiphase flow processes to enable improved design and increased operational efficiency of existing and new processing equipment. Characteristics used to predict performance of multiphase processes may include, for example, spatial distribution of the phases (spatial volumetric phase fractions), flow regime, interfacial area, and absolute and relative velocities between the phases or materials. Knowing the spatial distribution of the materials is particularly useful because non-uniform distribution of the materials tends to reduce the interfacial area between materials available for chemical reaction or conversion and may result in recirculating flows creating spatially non-uniform reaction zones or concentrations. Further, the volumetric phase fraction and velocity are important parameters that enable proper and timely control of multiphase flows.

Electrical-impedance tomography (EIT) is a minimally invasive measurement technique that can be used to quantitatively map material distributions within multi-material objects. In EIT, a map of the electrical conductivity and permittivity is used to infer the distribution of different materials within a multi-material object. Different current patterns or voltage patterns are applied to the object through electrodes surrounding the object, and the corresponding voltages or currents are measured. Based on the current-voltage relations, an internal impedance or internal admittance distribution is determined.

Image reconstruction based on the calculated impedance distribution using various image processing algorithms is one method by which distribution of different materials within the multi-material object is determined. However, image-processing algorithms are often too time-consuming and computationally intensive. They also ignore many qualitative aspects of the problem such as spatial symmetry or asymmetry.

Therefore, it is desirable to determine a method and a system that will address the foregoing issues.

BRIEF DESCRIPTION

In accordance with an embodiment of the present invention, a method for determining characteristics of a multi-material object is provided. The method includes determining an electric element matrix representing the multi-material object and pre-multiplying the electric element matrix with a first mathematical transformation matrix to obtain a first transformed electric element matrix. The method also includes post-multiplying the first transformed electric element matrix with a second mathematical transformation matrix to obtain a second transformed electric element matrix. The method further includes determining the characteristics of the multi-material object based on the second transformed electric element matrix.

In accordance with another embodiment of the present invention a multi-material sensing system is provided. The system includes a power supply for providing an applied electrical signal set to electrodes surrounding a multi-material object and a measurement unit for obtaining a measured electrical signal set from the electrodes. The system further includes a processing circuitry for determining an electric element matrix based on the applied and the measured signal sets and for pre-multiplying the electric element matrix with a first mathematical transformation matrix to obtain a first transformed electric element matrix. The processing circuitry further post-multiplies the first transformed electric element matrix with a second mathematical transformation matrix to obtain a second transformed electric element matrix and determines the characteristics of the multi-material object based on the second transformed electric element matrix.

In accordance with yet another embodiment of the present invention, a method for determining characteristics of a multi-material object is provided. The method includes providing an applied electrical signal set to the electrodes surrounding the multi-material object and obtaining a measured electrical signal set of measured electrical signals from the electrodes. The method further includes pre-multiplying the measured electrical signal set with a first mathematical transformation matrix to obtain a first transformed measured electrical signal set and post-multiplying the first transformed measured electrical signal set with a second mathematical transformation matrix to obtain a second transformed measured electrical signal set. The method also includes determining the characteristics of the multi-material object based on the second transformed measured electrical signal set.

DRAWINGS

These and other features, aspects, and advantages of the present invention will become better understood when the following detailed description is read with reference to the accompanying drawings in which like characters represent like parts throughout the drawings, wherein.

Figure 8:
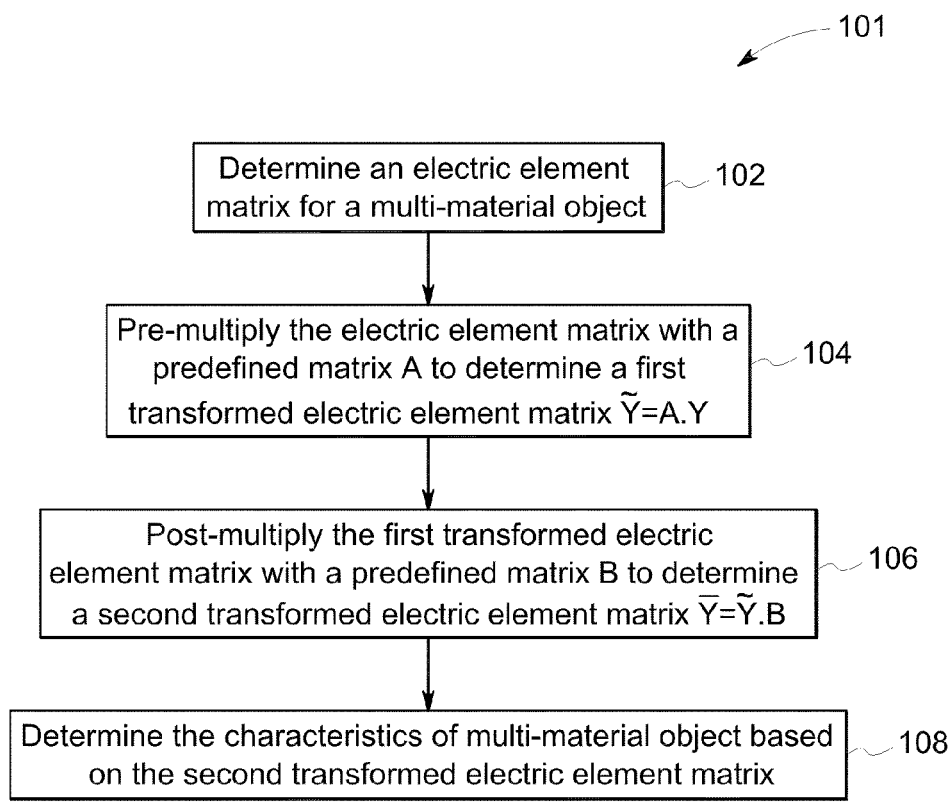
Figure 9:
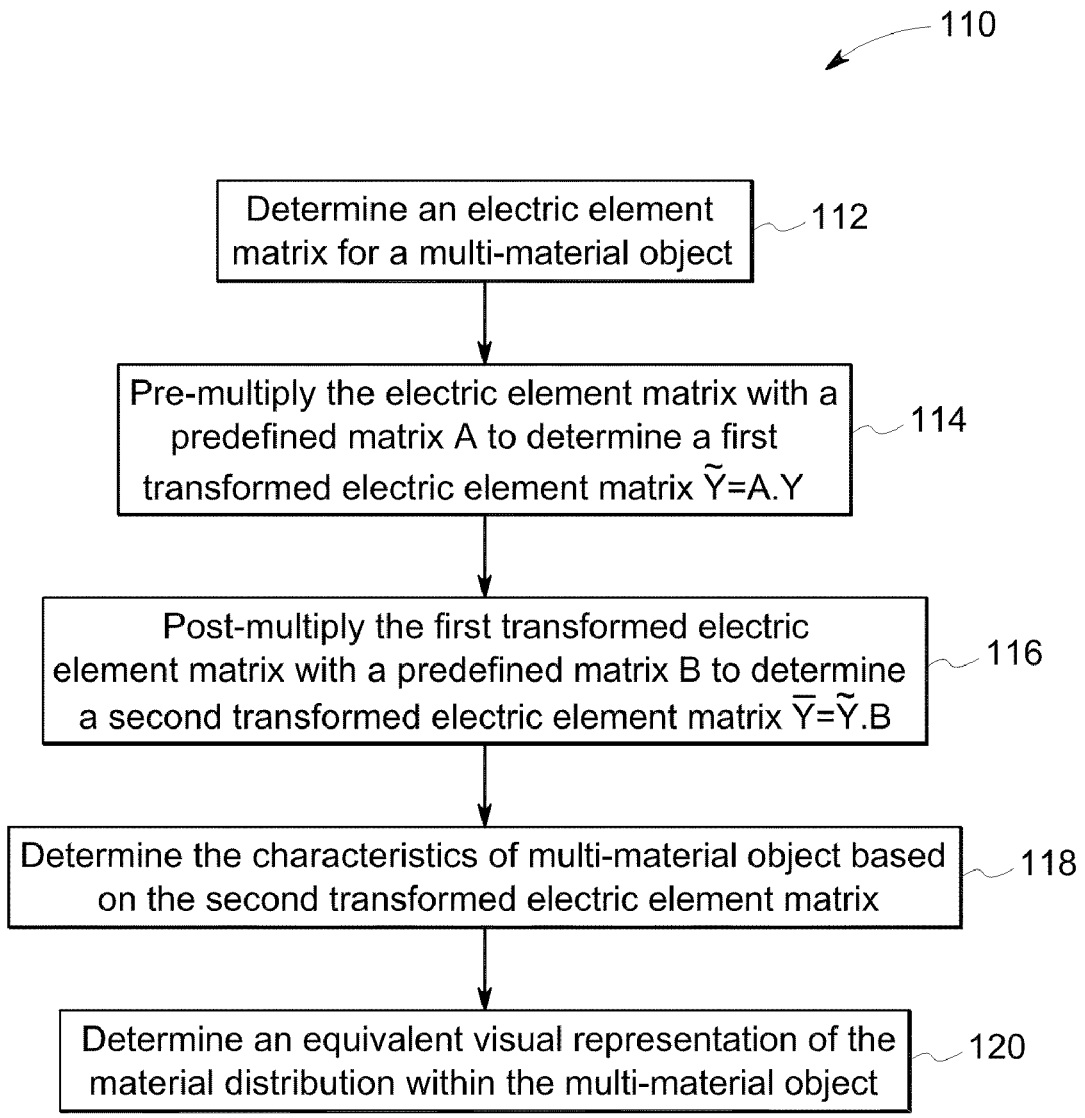
Figure 10:
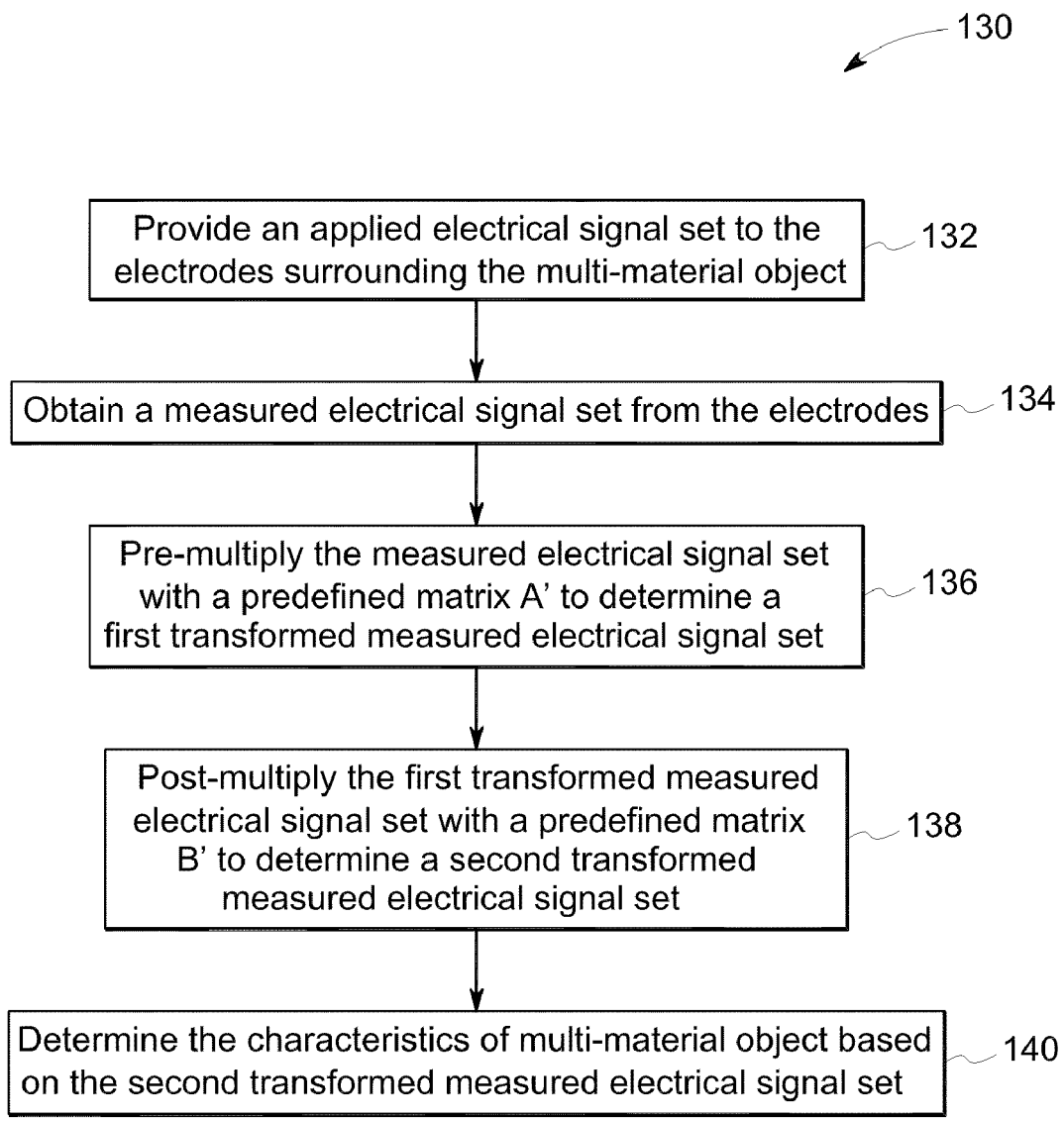

FIG. 8 is a flow chart representing a method of determining characteristics of a multi-material object in accordance with an embodiment of the present invention; and FIG. 9 is a flow chart representing an analysis of a multi-material object in accordance with an embodiment of the present invention; and FIG. 10 is a flow chart representing a method of determining characteristics of a multi-material object based on an electrical signal set in accordance with an embodiment of the present invention.

DETAILED DESCRIPTION

As discussed in detail below, embodiments of the present invention function to provide a system and a method for measuring the characteristics of a multi-material object. In an example of a multiphase flow, the characteristics of the object may include volumetric fractions and flow rates of oil, water, and gas (in this context referencing gaseous hydrocarbons) flowing through conduits. Although the invention is described with reference to a use in oil/gas/water measurements, it is by no means limited to such applications; rather, aspects of the invention find application in a wide variety of industrial, healthcare and chemical processes such as, cancer diagnosis and water treatment processes. The characteristics of such multi-material objects may be quite different from the examples given for multiphase flow.

Figure 1:
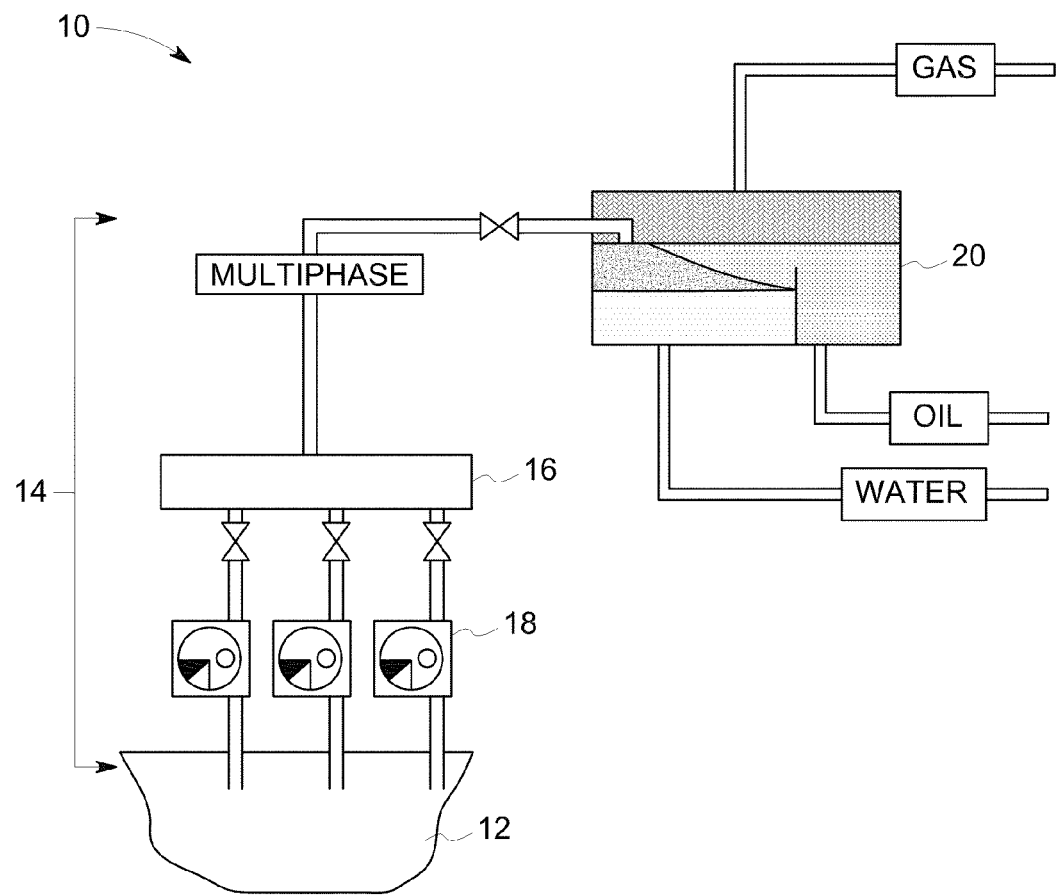
FIG. 1 is a block diagram of a oil production facility according to an example embodiment.

FIG. 1 shows an oil production facility 10 according to an example embodiment. The oil production facility typically includes multiple oil wells 12 that are each interconnected to a piping system 14. The piping system 14 includes a production manifold 16 coupled to multiphase flow meters (MPFMs) 18. A multiphase flow meter enables measurement of unprocessed well streams very close to the well and thus can provide continuous monitoring of well performance, which may be used for better reservoir management. Fluids pumped from oil wells 12 are sent to a production separator 20 through the production manifold 16. It should be noted that a test separator (not shown) may additionally be used along with MPFMs in the facility 10 or may alternatively be used. One advantage of a MPFM over a test separator is the reduction in time needed to perform a measurement. While the test separator must be allowed to fill and stabilize when changing wells, the MPFM responds more quickly to changes in well fluids and needs less time to stabilize.

The production separator 20 separates oil, gas, and water pumped from the wells. The production separator 20 may include one or more measurement devices. The measurement devices may include, for example, a water meter to measure an amount or rate of water extracted from a well and an emulsion meter to measure an amount of oil extracted from the well. Further measurement devices may include other devices typically utilized to monitor well performance such as a wellhead pressure sensor, thermometer, salinity meter and a pH meter.

Figure 2:
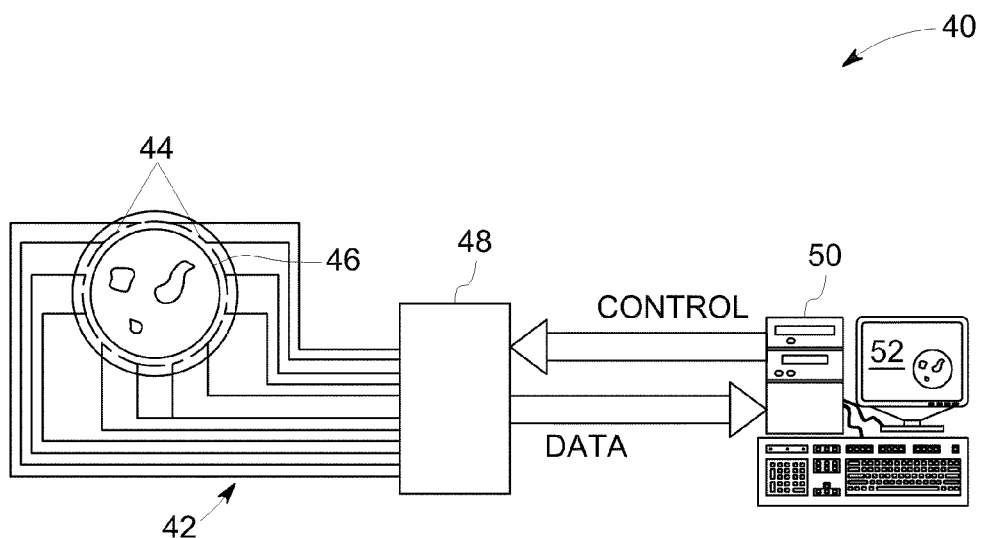
FIG. 2 is a schematic of an electrical impedance tomography (EIT) based multiphase flow meter to be used in accordance with an embodiment of the present invention.

FIG. 2 shows an electrical impedance tomography (EIT) based MPFM system 40. In EIT, the conductivity or permittivity distribution within a multi-material object is inferred from electrical measurements made through electrodes surrounding the object. Conducting electrodes are attached to the periphery of the multi-material object and alternating currents or voltages are applied to some or all of the electrodes. The resulting electrical potentials or currents respectively are measured, and the process is repeated for numerous different configurations or patterns of applied currents and/or voltages.

The MPFM system 40 of FIG. 2 includes an electrode array 42 comprising a number of electrodes 44 distributed around a conduit 46. The conduit may comprise a container, which carries multiple materials or phases within it, such as a pipe or tank, or the conduit may comprise another vessel such as a part of a human body or an entire human body. In a more specific embodiment, the number of electrodes may be eight, twelve or sixteen, depending on the size of the conduit and the accuracy needed. The electrodes may be attached directly to the inside wall of the conduit with one embodiment including use of a suitable coating to ensure good electrical contact, if needed. The electrodes are connected to electronic conditioning circuitry 48, which may include components such as a current or voltage source, D-to-A-converters, A-to-D converters, differential amplifiers, filters, digital multiplexers, analog multiplexers, a clock, and/or a digital I/O unit coupled to a computer 50. Computer 50 comprises, in one embodiment, a personal computer equipped with a digital signal processor card used for the image reconstruction process and a suitable display 52 for displaying the images. Other processing circuits such as a field-programmable gate array (FPGA) or a complex programmable logic device (CPLD) may also be used in other embodiments. In accordance with an embodiment of the present invention, electrodes 44 are stimulated by applying a voltage set of voltage patterns across them, which produces rotating electric field within the multi-material object in the conduit. At any given time, one or more voltage sources are used to apply one pattern of voltages to the electrodes, and the corresponding set of current signals in each of the electrodes is measured. In one embodiment, instead of applying voltages, one or more current sources are used to stimulate the electrodes by injecting currents into them, and corresponding voltages are measured across the electrodes.

Figure 3:
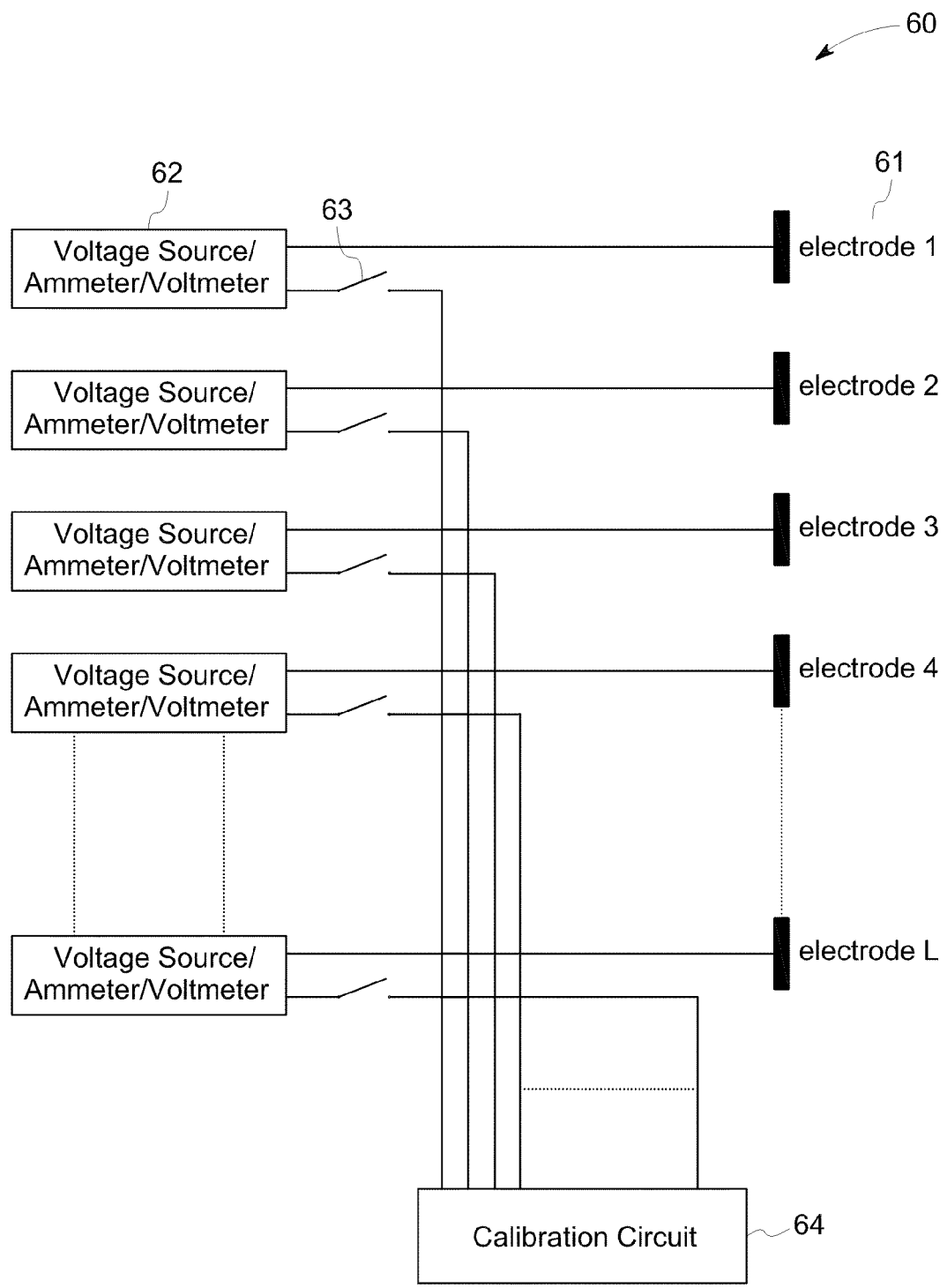
FIG. 3 is a block diagram of an applied-voltage EIT system in accordance with an embodiment of the present invention.

FIG. 3 is a block diagram 60 of an applied-voltage EIT system with L electrodes. Each electrode 61 is connected to a circuit that includes a voltage source 62 for generating the applied voltage as well as an ammeter to measure the applied current and a voltmeter to directly measure the applied voltage. A switching network 63 enables a single calibration circuit 64 to be connected to any of the voltage source/ammeter/voltmeter circuits to allow the whole system to be calibrated to a single reference. A digital controller (not shown) may be interfaced to the voltage sources (with ammeters and voltmeters), switches, and the calibration circuit may be used to set the system configurations and collect digital measurements of voltage and current. In another embodiment wherein currents instead of voltages are applied to the electrodes, the currents are generated using current sources, which may comprise direct current sources or a system of voltage-to-current converters, for example.

In both of the current and voltage source embodiments, the resulting measurements are processed by the computer 50 (FIG. 2), and the representation of the electrical impedance or admittance distribution within the multi-material object is determined. The electrical impedance or admittance distribution is then further analyzed by the computer 50 to provide characteristics of the multi-material object. Characteristics of the multi-material object may include, for example, composition and distribution of materials of the system. Further, the electrical impedance or admittance distribution may also be analyzed to determine flow regimes, phase fraction, and velocity of individual materials of the multi-material object. The flow regimes may include but are not limited to bubbly flow, churn flow, slug flow, or annular flow, for example.

In voltage source embodiments, the current flowing from one electrode to another is a function of relative voltages applied across all electrodes and the conductivity and permittivity of the materials present between all the electrodes. For example, the material may be only oil or it may be a mixture of oil and gas. Depending on the materials and their distribution, the impedance or admittance between all the electrodes varies, and the current flowing between electrodes also varies. Thus, from the applied voltage set and the measured current set, the impedance set or impedance matrix of impedances between every pair of electrodes can be calculated. Similarly, from the applied voltage set and the measured current set, the admittance set or admittance matrix of impedances between every pair of electrodes can alternatively or additionally be calculated. Because impedance and admittance are a function of the conductivity and the permittivity of the materials between electrodes, by analyzing the impedance or admittance network, the material distribution and its characteristics may be determined. Several methods can be employed to compute the impedance or admittance matrix from the applied electrical signal set and the measured electrical signal set. These methods may include but are not limited to using a pseudo-inverse or an iterative algorithm. In one embodiment, it is possible to analyze the measured electrical signal set of electrical signals from electrodes and determine the characteristics of the multi-material object. The measured electrical signals may comprise voltage signals or current signals. It should be noted that since the measured electrical signals are also a function of conductivity and the permittivity of the materials between electrodes, in one embodiment, it is possible to analyze the characteristics of the multi-material object by analyzing the measured electrical signal set of measured electrical signals.

In an embodiment of the present invention, the analysis of an admittance network includes pre-multiplying the impedance or the admittance matrix Y with a first mathematical transformation matrix A and post-multiplying the resultant product matrix by a second mathematical transformation matrix B as given by equation (1). Thus, a transformed impedance or admittance matrix is represented by $\overline{Y}$ and is given as:

$$\overline{Y} = A \times Y \times B \tag{1}$$

The matrix Y and $\overline{Y}$ may have an L number of rows and an L number of columns, where L is the number of electrodes. In certain embodiments, it is possible to truncate the impedance and admittance matrix by one or more rows or columns depending upon prior information on the materials within the object in the interest of faster processing. The matrices A and B may or may not be related to each other. Further, the matrices A and B would have appropriate number of rows and columns so that the multiplications as shown in equation (1) may be achieved. It will be appreciated by those skilled in the art that pre-multiplication refers to multiplication on left and post-multiplication refers to multiplication on right as shown in equation (1).

Depending upon matrices A and B, the multiplication of matrix Y with A and B may transform the coordinate system or convert the impedance or admittance matrix into a spatial Fourier transform domain. In one embodiment, the matrices A and B given in equation (1) may by themselves be the product of several matrices. In another embodiment, the matrix A or B may be an identity matrix. In yet another embodiment, the matrices A and B in equation (1) may be the L-point Discrete Fourier Transform (DFT) matrix and its inverse respectively. If the DFT matrix A and its inverse B are represented by C and $C^{-1}$ respectively, equation (1) can be modified as:

$$\overline{Y} = C \times Y \times C^{-1} \tag{2}$$

The element at the $m^{th}$ row and $n^{th}$ column in matrix C can be given as:

$$C(m,n) = a^{(m-1)(n-1)} \tag{3}$$

where $a = e^{(-2\pi i/L)}$, e is Euler's constant, i is the square root of $-1$ and L is the number of energized electrodes. The energized electrodes refer to the electrodes to which voltage signals or current signals are applied. In one embodiment there may be 8 electrodes out of which only 4 electrodes are energized. The values of m and n vary from 0 to a maximum of L−1. Thus, for a four-electrode system, C is given by equation (4) below $$C = \frac{1}{2} \begin{bmatrix} 1 & 1 & 1 & 1 \\ 1 & -i & -1 & i \\ 1 & -1 & 1 & -1 \\ 1 & i & -1 & -i \end{bmatrix} \tag{4}$$

The various elements of the transformed matrix $\overline{Y}$ contain useful information on the characteristics of the multi-material object. Qualitatively, the diagonals of the transformed impedance matrix represent the spatial symmetry in the distribution of the materials within the multi-material object and the off-diagonal elements represent the asymmetry in the distribution of materials within the multi-material object. All the elements in the first column and the first row of the matrix $\overline{Y}$ typically have a value of zero except in the case where there may be an alternate path for the passage of electric current apart from the electrodes used. Therefore, the elements in the first row and first column of $\overline{Y}$ can be used as indicators for the presence of leakage currents and alternate paths for such currents or the existence of ground faults in the EIT system. It should be noted that in one embodiment, $\overline{Y}$ may contain time varying elements. However, since the matrix $\overline{Y}$ is analyzed continuously in real time, it will have no effect in determining the characteristics of the multi-material object. As mentioned earlier, in one embodiment, it is possible analyze a measured electrical signal set of measured electrical signals and determine the characteristics of the multi-material object. In such an embodiment, the measured electrical signal set is mathematically transformed and based on elements of the transformed measured electrical signal set the characteristics of the multi-material object are determined. Mathematically, the only difference in this embodiment is that in equation (2), the matrix Y will be replaced by the measured electrical signal set i.e. voltage matrix or current matrix.

Figure 4:
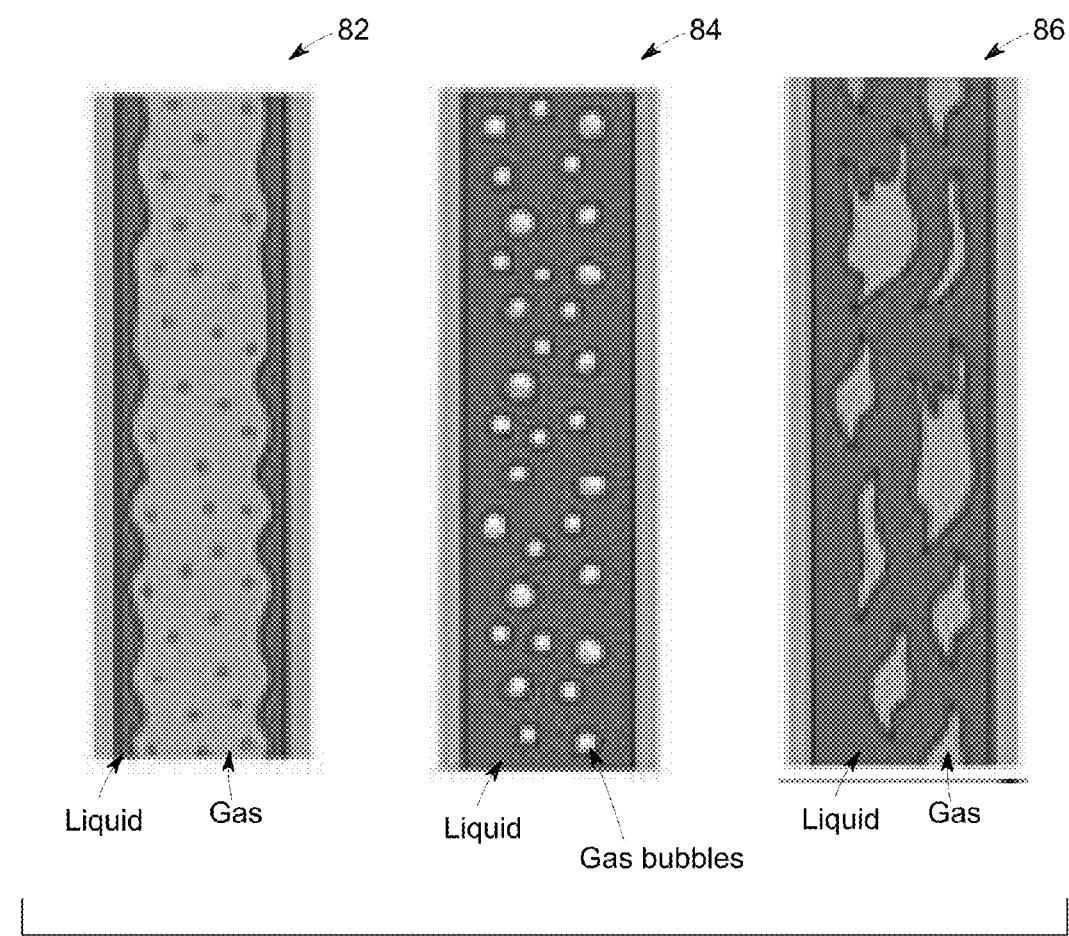
FIG. 4 is representation of three different flow regimes of a mixture of two phase components.

FIG. 4 shows three different regimes as a mixture of two materials flows through a conduit. The two phases in the example of FIG. 4 include a gas and a liquid. Flow regime 82 is an annular flow regime where the gas phase tends to move through the center of the conduit and the liquid phase forms an annulus around the gas phase. Flow regime 84, for example, is a bubbly flow and is characterized by the gas phase being distributed as bubbles through the liquid phase. Flow regime 86 is a representation of churn flow and is characterized by oscillatory, up and down motions of the liquid. There are several other flow regimes that are possible depending upon the orientation of the conduit with respect to gravity of the earth. It should be noted that these flow regimes tend to produce a specific distribution of the materials within the conduit. These distributions may be quantified to have a specific, time-varying signature in terms of its spatial symmetry and spatial asymmetry.

The different elements of the matrix $\overline{Y}$ can be used to identify various flow regimes. For example, the flow can be said to be spatially symmetric when a single homogenous material flows through the conduit. In this case, except the elements along the diagonal of the matrix $\overline{Y}$ i.e. off-diagonal elements, all the elements have a value of zero. In the absence of ground faults or leakage currents, the element in the first row and first column may also be zero. For a four electrode EIT and spatially symmetric flow, the matrix $\overline{Y}_{symmetric}$ may be written as:

$$\overline{Y}_{symmetric} = \begin{bmatrix} 0 & 0 & 0 & 0 \\ 0 & a & 0 & 0 \\ 0 & 0 & b & 0 \\ 0 & 0 & 0 & c \end{bmatrix} \quad (5)$$

The values of a, b and c in equation (5) would scale up or down linearly depending upon the electrical properties of the homogenous material flowing through the conduit. Hence, the values of a, b and c in equation (5) may be used to determine the electrical properties of the homogenous material within the conduit.

In another embodiment, when the flow regime is symmetrically annular, it can be said that the material distribution is spatially symmetric. Again, except the elements along the diagonal of the matrix $\overline{Y}$, all the other elements would be zero as shown by $\overline{Y}_{annular}$ matrix below:

$$\overline{Y}_{annular} = \begin{bmatrix} 0 & 0 & 0 & 0 \\ 0 & a' & 0 & 0 \\ 0 & 0 & b' & 0 \\ 0 & 0 & 0 & c' \end{bmatrix} \quad (6)$$

However, apart from the absolute values of the non-zero diagonal elements, a ratio of the different diagonal elements would provide an estimation of the size of the annulus. It should be noted that the elements along the diagonal in equation (6), of a', b' and c', are different from the case where a single homogenous material flows through the conduit.

In yet another embodiment, where the flow regime is bubbly, it can be said that the flow is not spatially symmetric and a good degree of asymmetry is present. In this case, the elements in the matrix $\overline{Y}$, except those present in the first row and first column may be non-zero as given by $\overline{Y}_{bubbly}$ matrix below:

$$\overline{Y}_{bubbly} = \begin{bmatrix} 0 & 0 & 0 & 0 \\ 0 & a'' & f & m \\ 0 & x & b'' & n \\ 0 & y & g & c'' \end{bmatrix} \quad (7)$$

The elements along the diagonal in equation (7), a", b" and c", are different from the case where a single homogenous material flows through the conduit. The absolute and relative values of the diagonal and non-diagonal elements can be used to identify the flow regime.

Figure 5:
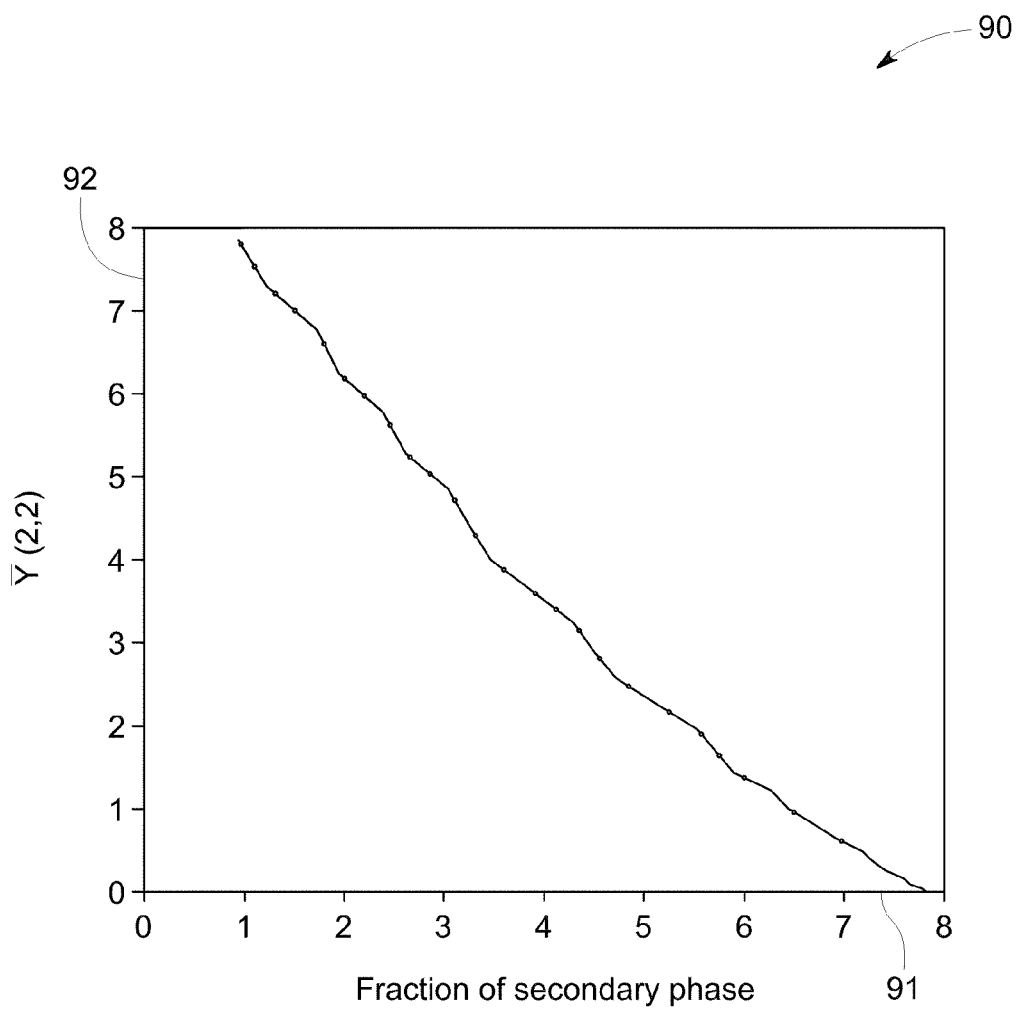
FIG. 5 is a graphical representation of the variation of a matrix element $\overline{Y}$ (2,2) with a fraction of a secondary phase.

FIG. 5 shows a plot 90 of variation of the element at the second row and second column of the matrix $\overline{Y}$, called $\overline{Y}$ (2,2), with increasing fraction of the secondary phase or material. The horizontal axis 91 represents the phase fraction of secondary phase and the vertical axis 92 represents values of element (2,2) of the matrix $\overline{Y}$. Thus, if the plot is stored in the computer, then by comparing the value of element (2,2) of the calculated matrix $\overline{Y}$ with the stored plots, the phase fraction in the system can be determined.

Figure 6:
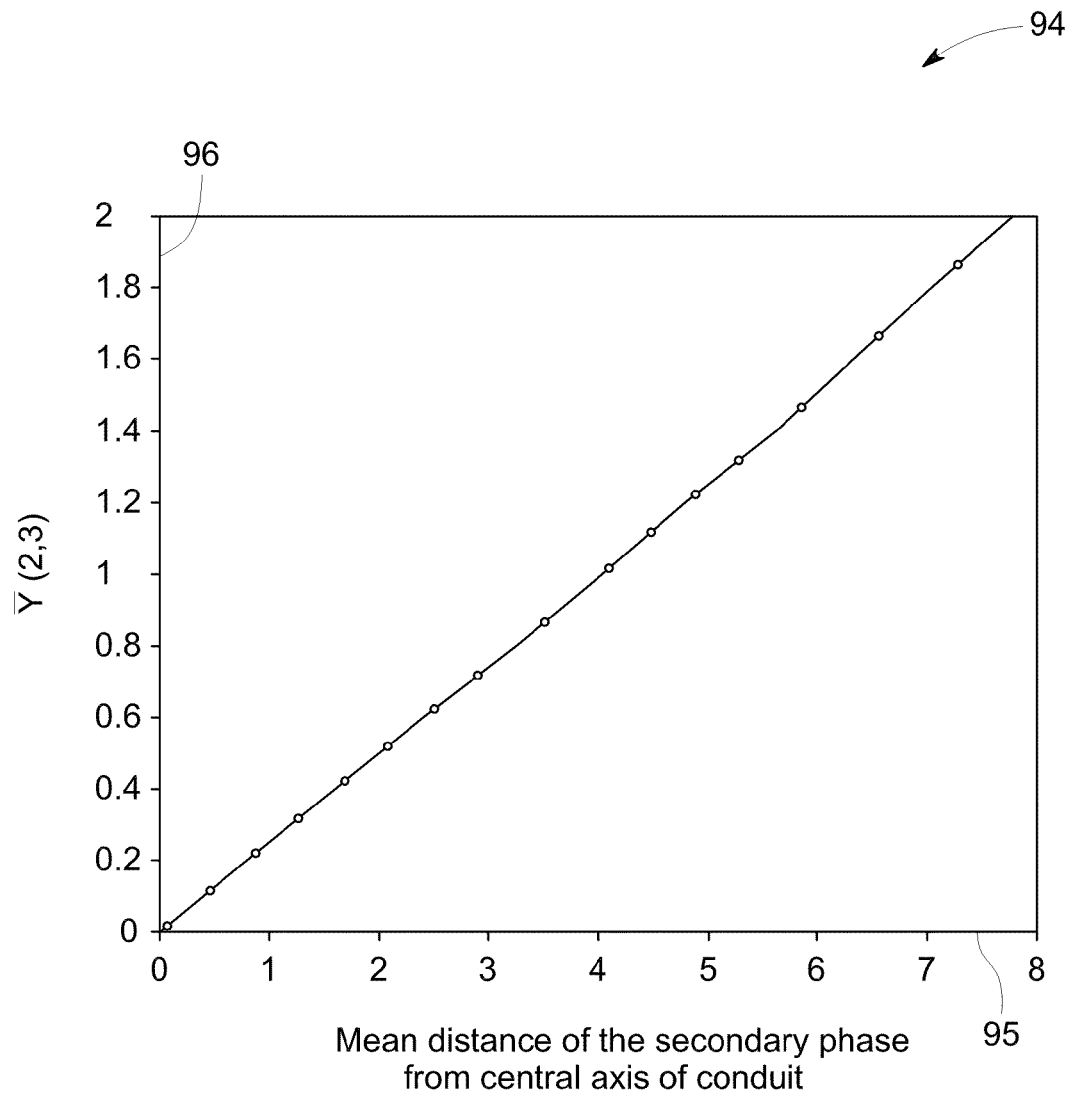
FIG. 6 is a graphical representation of the variation of a matrix element $\overline{Y}$ (2,3) with mean distance of the secondary phase from central axis of conduit.

FIG. 6 shows a plot 94 of variation of the element at the second row and third column in matrix $\overline{Y}$, called $\overline{Y}$ (2,3) with increasing mean distance of the fraction of the secondary phase or material from the central axis of the conduit. The horizontal axis 95 represents the mean distance of the secondary phase from the central axis of the conduit and the vertical axis 96 represents the values of element (2,3) of the matrix $\overline{Y}$. Again, if these plots are stored in the computer, then in real time the mean distance of a concentrated bubble from the center of the pipe can be determined by comparing the value of element (2,3) of the calculated matrix $\overline{Y}$ with the stored plots.

The data shown in FIG. 5 and FIG. 6 may be obtained by several numerical simulations of randomly generated flow regimes and material distributions within the conduit that may be corrected based on experimental results. The values of other elements within the $\overline{Y}$ matrix for different flow regimes and material distributions may be numerically calculated and/or empirically corrected. It should be noted that the other elements may have non-linear relations to the original distribution unlike the linear relationships shown in the graphs in FIG. 5 and FIG. 6.

Figure 7:
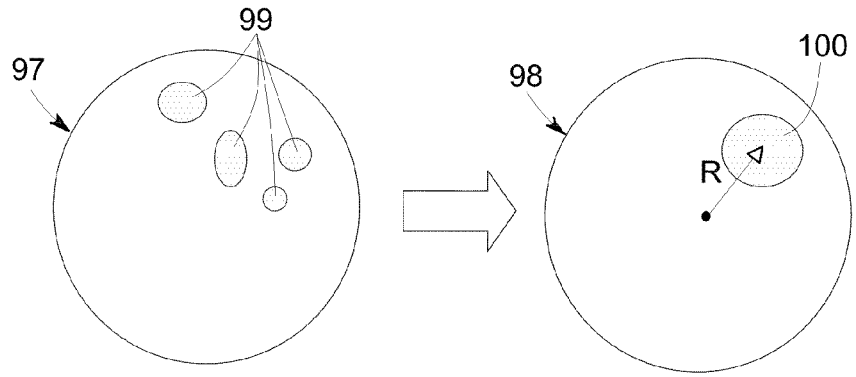
FIG. 7 is a graphical representation of the an original distribution and its equivalent distribution of the secondary phase in accordance with an embodiment of the present invention.

FIG. 7 shows an original distribution 97 and its equivalent distribution 98 of the secondary phase visualized from the behavior of the various elements of the $\overline{Y}$ matrix in accordance with an embodiment of the present invention. The original distribution 97 shown, for example is a bubbly flow distribution. From the current and voltage measurements made on electrodes placed around the conduit carrying this bubbly distribution, a Y matrix and subsequently a $\overline{Y}$ matrix may be computed. As already shown, the element $\overline{Y}$ (2,2) represents the total fraction occupied by the secondary phase in the plane of the electrodes and $\overline{Y}$ (2,3) represents the mean distance of the secondary phase from the central axis of the conduit. From these two elements of the $\overline{Y}$ matrix, it is possible to equivalently represent the material distribution within the conduit as shown in the equivalent distribution 98. In the equivalent distribution 98, various distributed areas 99 of the secondary phase are combined into a single area 100 and the mean distance of the single area of the secondary phase from the central axis of the conduit is shown by a variable R. It should be noted that the equivalent representation of the materials within the conduit is different from the result a full image processing or reconstruction algorithm would produce using the current and voltage information. The advantage of the equivalent distribution 98 is that while being a visual method of representing the original material distribution within the conduit, it does not increase the computation needed significantly.

In one embodiment, the elements of the $\overline{Y}$ matrix from one or more sets of electrodes provide an indication of the velocity and density of various phases or materials within the conduit. These models may be coupled with numerical fluid dynamics models and electromagnetic models of multiphase flow in order to predict and correct the measurements in real-time.

FIG. 8 is a flow chart 101 for a method of determining the characteristics of a multi-material object in accordance with one embodiment of the present invention. The method includes determining the electric element matrix representing the multi-material object in step 102. This can be achieved by a number of methods and may involve using the pseudo-inverse of an applied or measured electrical signal set, for example. In step 104, the electric element matrix is pre-multiplied by a predefined first mathematical transformation matrix A to compute a first transformed electric element matrix. In step 106, the first transformed electric element matrix is post-multiplied by a predefined second mathematical transformation matrix B to compute a second transformed electric element matrix. In step 108, the characteristics of the multi-material object are determined from the analysis of the second transformed electric element matrix. The electric element matrix could be an impedance matrix or an admittance matrix representing the multi-material object, for example.

FIG. 9 is a flow chart 110 for an analysis of a multi-material object that can be performed in accordance with one embodiment of the present invention. The method includes determining electric element matrix representing the multi-material object in step 112. In step 114, the electric element matrix is pre-multiplied by a predefined first mathematical transformation matrix A to compute a first transformed electric element matrix. In step 116, the first transformed electric element matrix is post-multiplied by a predefined second mathematical transformation matrix B to compute a second transformed electric element matrix. In step 118, the characteristics of the multi-material object are determined from the analysis of the second transformed electric element matrix. In step 120, an equivalent visual representation of the material distribution within the multi-material object is determined and displayed. One example of the equivalent visual representation is shown in FIG. 7.

FIG. 10 is a flow chart 130 for a method of determining the characteristics of a multi-material object based on an electrical signal set in accordance with an embodiment of the present invention. Since the electric element matrix can be determined from applied electrical signals and measured electrical signals, in one embodiment, it is possible to directly determine the characteristics of a multi-material object from the applied electrical signal set and the measured electrical signal set. The method includes providing an applied electrical signal set to the electrodes surrounding the multi-material object in step 132. In step 134, a measured electrical signal set of measured electrical signals from the electrodes is obtained. In one embodiment, a current matrix I of measured current signals or a voltage matrix V of measured voltage signals from the electrodes is used directly (instead of having the intermediate step of forming the electric element matrix) to determine characteristics of the multi-material object. The currents are measured when voltages are applied to electrodes and voltages are measured when currents are applied to the electrodes. In step 136, the measured electrical signal set is pre-multiplied by a predefined first mathematical transformation matrix A' to compute a first transformed measured electrical signal set. In step 138, the first transformed second electrical signal set is post-multiplied by a predefined second mathematical transformation matrix B' to compute a second transformed measured electrical signal set. In such a case, the matrices A' and B' will have different values compared to A and B of method described in FIG. 8. In step 140, the characteristics of the multi-material object are determined from the analysis of the second transformed measured electrical signal set.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system for determining characteristics of a multi-material object comprising:
    a measurement unit to obtain a measured electrical signal set from electrodes surrounding the multi-material object; and
    a processing circuitry configured to perform steps of:
        determining an electric element matrix representing the multi-material object based on the measured electrical signal set;
        pre-multiplying the electric element matrix with a first mathematical transformation matrix to obtain a first transformed electric element matrix;
        post-multiplying the first transformed electric element matrix with a second mathematical transformation matrix to obtain a second transformed electric element matrix; and
        determining the characteristics of the multi-material object based on the second transformed electric element matrix,
    wherein the characteristics of the multi-material object comprise compositions and distributions of different materials within the multi-material object.

2. The system of claim 1, wherein the electric element matrix comprises an impedance matrix or an admittance matrix.

3. The system of claim 1, wherein the first mathematical transformation matrix and the second mathematical transformation matrix transform a coordinate system of the electric element matrix.

4. The system of claim 1, wherein the first mathematical transformation matrix comprises a discrete Fourier transform matrix and the second mathematical transformation matrix comprises an inverse of the discrete Fourier transform matrix.

5. The system of claim 1, wherein the first mathematical transformation matrix comprises an identity matrix.

6. The system of claim 1, wherein the second mathematical transformation matrix comprises an identity matrix.

7. The system of claim 1, wherein determining the characteristics of the multi-material object comprises determining a spatial symmetry in the distribution of the materials within the multi-material object based on the elements along a diagonal of the second transformed impedance matrix and determining an asymmetry in the distribution of materials within the multi-material object based on the elements that do not lie along the diagonal of the second transformed impedance matrix.

8. The system of claim 1, wherein determining the characteristics of the multi-material object comprises determining a presence of current paths other than current paths through energized electrodes surrounding the multi-material object based on elements in the first row and the first column of the second transformed electric element matrix.

9. The system of claim 1, wherein determining the characteristics of the multi-material object comprises utilizing the information of the electric element matrix obtained from numerical simulations of randomly generated flow regimes and material distributions.

10. The system of claim 1, wherein determining the characteristics of the multi-material object comprises utilizing the information on the electric element matrix based on prior experimental results.

11. The system of claim 1, wherein elements not lying on a diagonal of the electric element matrix comprise zeros for a spatially symmetric flow regime.

12. The system of claim 11, wherein the spatially symmetric flow regime comprises at least one of a churn flow regime or an annular flow regime.

13. The system of claim 1, wherein elements not lying on a diagonal of the electric element matrix comprise non-zero values for an asymmetric flow regime.

14. The system of claim 13, wherein the asymmetric flow regime comprises a bubbly flow regime.

15. The system of claim 1, wherein determining the characteristics of the multi-material object comprises determining flow regimes, volumetric fraction, density and velocity of the materials within the multi-material object.

16. The system of claim 1, wherein the processing circuitry is further configured for determining an equivalent visual representation of the material distribution within the multi-material object.

17. The system of claim 16, wherein determining the characteristics of the multi-material object comprises determining flow regimes, volumetric fraction, density and velocity of the materials within the multi-material object based on the equivalent visual representation.

18. The system of claim 16, wherein determining the equivalent visual representation of the material distribution within the multi-material object comprises combining various distributed areas of the secondary phase into a single area.

19. A multi-material sensing system comprising:
a power supply to provide an applied electrical signal set to electrodes surrounding a multi-material object;
a measurement unit to obtain a measured electrical signal set from the electrodes; and
processing circuitry to determine an electric element matrix based on the applied and measured electrical signal sets, to pre-multiply the electric element matrix with a first mathematical transformation matrix to obtain a first transformed electric element matrix, to post-multiply the first transformed electric element matrix with a second mathematical transformation matrix to obtain a second transformed electric element matrix and to determine the characteristics of the multi-material object based on the second transformed electric element matrix,
wherein the characteristics of the multi-material object comprise compositions and distributions of different materials within the multi-material object.

20. The system of claim 19, wherein the power supply comprises a voltage source or a current source.

21. The system of claim 19, wherein the measurement unit comprises a voltmeter or a current meter.

22. The system of claim 19, wherein the multi-material object comprises oil, water, and gas.

23. A non-transitory computer-readable medium comprising computer-readable instructions of a computer program that, when executed by a processor, cause the processor to perform a method of determining characteristics of a multi-material object comprising:
providing an applied electrical signal set to the electrodes surrounding the multi-material object;
obtaining a measured electrical signal set of measured electrical signals from the electrodes;
pre-multiplying the measured electrical signal set with a first mathematical transformation matrix to obtain a first transformed measured electrical signal set;
post-multiplying the first transformed measured electrical signal set with a second mathematical transformation matrix to obtain a second transformed measured electrical signal set; and
determining the characteristics of the multi-material object based on the second transformed measured electrical signal set,
wherein the characteristics of the multi-material object comprise compositions and distributions of different materials within the multi-material object.

24. A system for determining characteristics of a multi-material object comprising:
a measurement unit to obtain a measured electrical signal set from electrodes surrounding the multi-material object; and
a processing circuitry configured to perform steps of:
determining an electric element matrix representing the multi-material object based on the measured electrical signal set;
pre-multiplying the electric element matrix with a first mathematical transformation matrix to obtain a first transformed electric element matrix;
post-multiplying the first transformed electric element matrix with a second mathematical transformation matrix to obtain a second transformed electric element matrix; and
determining the characteristics of the multi-material object based on the second transformed electric element matrix,
wherein the characteristics of the multi-material object comprise flow regimes, volumetric fraction, density and velocity of the materials within the multi-material object.

* * * * *